United States Patent [19]
Owen et al.

[11] 3,969,426
[45] July 13, 1976

[54] CONVERSION OF METHANOL TO PRODUCTS COMPRISING GASOLINE BOILING COMPONENTS

[75] Inventors: Hartley Owen, Belle Mead; Paul B. Venuto, Cherry Hill, both of N.J.

[73] Assignee: Mobil Oil Corporation, New York, N.Y.

[22] Filed: Oct. 17, 1974

[21] Appl. No.: 515,733

[52] U.S. Cl. .......................... 260/668 R; 260/671 R; 260/676 R; 260/677 R
[51] Int. Cl.$^2$ .................. C07C 15/04; C07C 15/06; C07C 1/20
[58] Field of Search ................ 260/668 R, 682, 676, 260/671 R, 677, 672 T, 668 A; 208/135, 141, 118, 120

[56] References Cited
UNITED STATES PATENTS 3,728,408  4/1973  Tobias............................ 260/668 C
3,856,873  12/1974  Burress........................... 260/672 T

*Primary Examiner*—D. Horwitz
*Attorney, Agent, or Firm*—Charles A. Huggett; Carl D. Farnsworth

[57] ABSTRACT

Methanol is converted in a plurality of conversion zones at temperatures selected from within the range of 500° to 1200°F. and reactant residence time within the range of 0.5 to 60 seconds in the presence of crystalline zeolite containing catalyst to particularly form products of desired volatility and octane in the gasoline boiling range. The distribution of methyl groups on $C_6+$ aromatics formed in the process to desired products is particularly accomplished under selected temperature and reactant contact time conditions.

15 Claims, 1 Drawing Figure

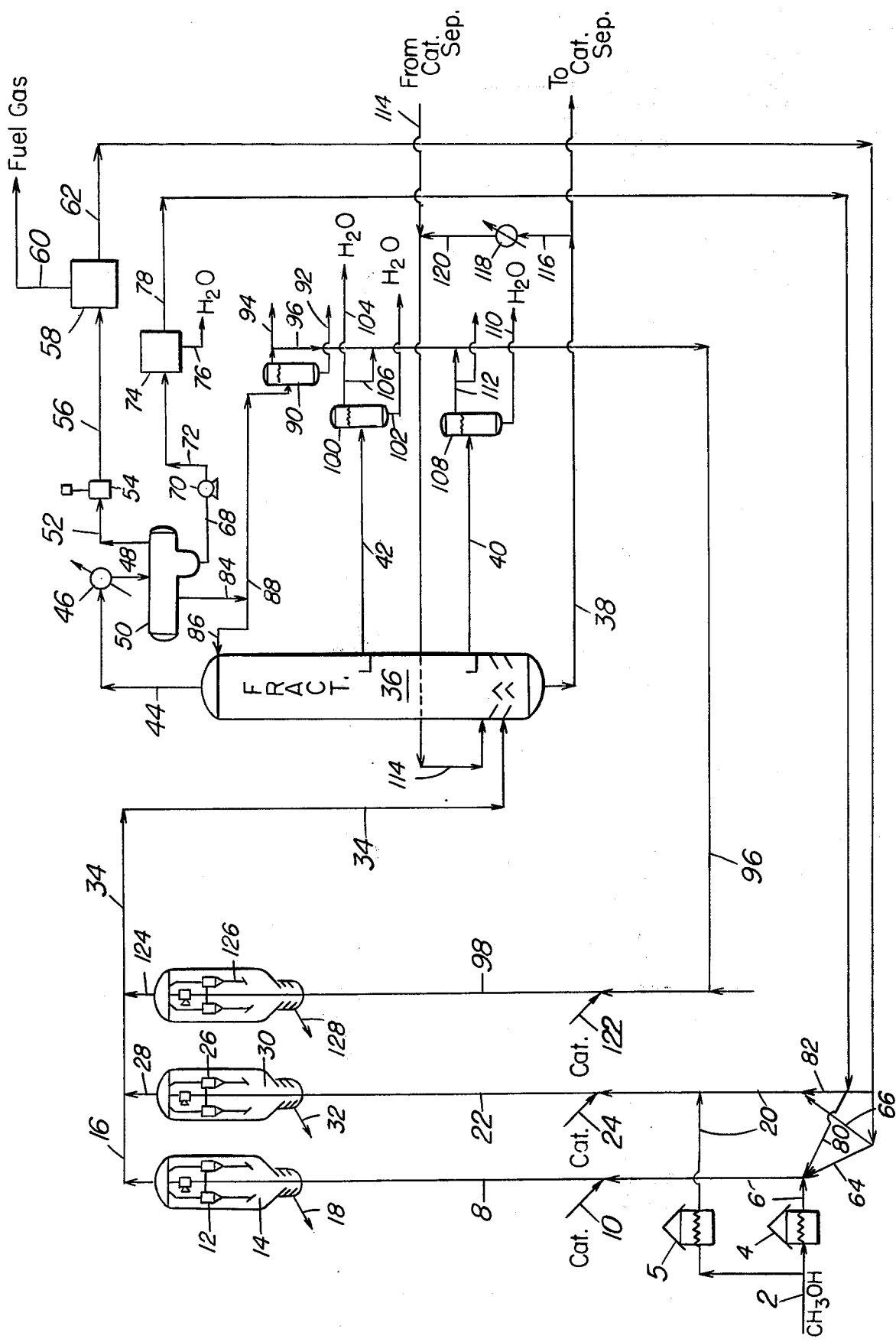

CONVERSION OF METHANOL TO PRODUCTS COMPRISING GASOLINE BOILING COMPONENTS

BACKGROUND OF THE INVENTION

In presently known catalytic processes for the conversion of methanol to gasoline boiling range components, it has been found that a great tendency exists to produce primarily high boiling liquid hydrocarbons, the major portion of which are found to exist as $C_6+$ materials comprising relatively high boiling aromatics and including durene quite often in an undesirable amount. Durene, for example, is an undesired high boiling aromatic which will crystallize out at low temperatures thus forming a solid film on heat exchanger tubes and process lines, often breaking up into a sludge which will plug lines through which it is passed. Thus the volatility profile of aromatics so formed and used as blending stocks is shifted to the upper or high boiling end of the gasoline boiling range. This undesired balance emphasizes the need for lighter high octane components comprising $C_5/C_6$ olefins and isoparaffins to provide front end volatility and octane in the gasoline product.

The present invention is concerned with the conversion of the lower alcohols to gasoline boiling components of particularly desired volatility and octane rating throughout the gasoline boiling range.

SUMMARY OF THE INVENTION

This invention relates to the method and catalyst employed for effecting the conversion of lower alcohols particularly methanol to high octane products boiling throughout the gasoline boiling range. To particularly effect the conversion operations of this invention, selective catalyst compositions comprising one or more crystalline zeolites alone or in combination with one another are relied upon for promoting the formation of desired products herein described. In a more particular aspect a feed comprising methanol is separated into two streams communicating with two separate reactant catalyst conversion zones which may be riser catalyst conversion zones permitting relatively short reactant residence time therein. One zone may be on the other hand, a dense fluid catalyst bed conversion zone.

In the combination of conversion zones above identified, and in accordance with this invention one riser conversion zone is employed to feature a high temperature conversion operation within the range of about 900° to about 1200°F. at relatively short reactant to catalyst contact time conversion within the range of 0.5 to 5 seconds in the presence of one or more crystalline zeolite conversion components suitable to produce a light, largely aliphatic product in the gasoline boiling range and providing improvement in the gasoline front end octane level. The second conversion zone, on the other hand, features a lower temperature conversion operation less than about 900°F. but above about 500°F. and more usually in the range of 700° to 800°F. at a longer reactant to catalyst contact time up to 10 or 60 seconds in the presence of one or more crystalline zeolite conversion components which will particularly provide under the lower temperature reaction conditions, a relatively high boiling and highly aromatic product boiling particularly in the gasoline boiling range. The relative reactant throughputs relied upon for each of the above specifically identified conversion operations is adjusted to provide a desired and proper balance with respect to product octane number, product volatility and a class of hydrocarbons particularly falling within a full boiling range gasoline product. By full boiling range gasoline product it is intended to include one boiling from about $C_5$ hydrocarbons up to about 400°F. Provisions for recycling unreacted alcohol, the ether product thereof, light olefins and other less desirable product components to either one or both reaction zones is contemplated and particularly discussed below.

In the combination operations herein identified, it is contemplated employing a catalyst with a cracking or acid function such as crystalline zeolite cracking catalysts. Preferred catalyst compositions contain a portion of an acidic solid such as one or more crystalline zeolite compositions intimately dispersed in a highly porous and relatively catalytically inert matrix material such as provided by a silica-clay-zirconia matrix. Zeolite compositions which may be employed are synthetic faujasite (X and Y types) and modified faujasites including dealuminized faujasite, rare-earth exchanged faujasites, hydrogen Y-type faujasites, stabilized faujasites, ZSM-4, ZSM-5 and ZSM-11 type crystalline zeolites, mordenite, TMA-mordenite, dealuminized mordenite, mordenite type, offretite, erionite, clinoptilolile, chabazite, gmelinite, levynite, sodalite and other small pore naturally occurring zeolite. Some preferred compositions are rare-earth exchanged faujasites particularly Y type crystalline faujasite, ZSM-5 type crystalline zeolites, mordenite type crystalline zeolites and dealuminized mordenite. A combination of two or more of the above crystalline zeolites may be employed. The crystalline zeolite may be a freshly prepared zeolite, steamed or unsteamed. It is preferred that the crystalline zeolite particle size be small, less than 5 microns and preferably less than 2 microns or it may be in the colloidal range. The zeolite component may be ion exchanged or otherwise modified prior to intimate admixture with the matrix. It is greatly preferred that the acidic zeolite crystallates have a total surface area of at least 10 meters square per gram (m 2/g) and more preferably from 100 to 800 meters square per gram.

The same catalyst may be employed in either reaction zone of the combination of reaction zones or a different catalyst may be used in each reaction zone. In operations using the ZSM-5 type crystalline zeolite alone it is contemplated cascading the catalyst from the higher temperature reaction zone to the lower temperature reaction zone for use therein alone or with other sources of catalyst passed to the second conversion zone such as recycled catalyst and/or freshly regenerated catalyst. On the other hand, when employing a different catalyst composition in each reaction zone, it is contemplated cascading ZSM-5 type catalytic material from the high temperature reaction zone to the lower temperature reaction zone in an amount sufficient to make up for losses of the crystalline component through attrition from the second reaction system.

The concepts, operating techniques and catalysts employed in the present invention are particularly directed to the production of full boiling range gasoline boiling components which will provide desired front end octane rating in conjunction with restricting the concentrations of benzene and undesired high boiling aromatics in the product obtained by the combination operation. The invention is also directed to the production of components of high purity finding particular application in the chemical industry.

In a more particular aspect it is contemplated using as a catalyst in a first reaction zone, a composite cracking catalyst containing a minor proportion up to about 15 wt.% of a modified faujasite zeolite such as a rare earth exchanged "Y" faujasite (REY) crystalline zeolite alone or the catalyst may contain other zeolites of smaller pore size in admixture therewith such as mordenite or a ZSM-5 type of crystalline zeolite. The catalyst for the second conversion zone is preferably a composite cracking catalyst containing a minor proportion of one or more of ZSM-5, ZSM-5 type zeolite, mordenite, erionite or other zeolites with molecular size-shape selective conversion properties dispersed in an inorganic matrix material of little or no cracking activity. The catalyst employed may be the same in each reaction zone as discussed above. Also the catalyst employed may be a dual function catalyst in that it provides a cracking function along with cyclization, polymerizing and an alkylation function in association with a metal hydrogenation function. Whatever catalyst is employed it should provide functions including the formation of carbon-hydrogen fragments used to restructure the lower alcohol, methanol, to form olefins, olefin oligomers, aromatics and alkylated aromatics boiling within the gasoline boiling ranges.

In view of the embodiments comprising the combination operation of this invention it is clear that these embodiments include the use of common and separate product recovery equipment as well as separate and common catalyst regeneration operations. However, since the combination operation of this invention is identified with a relatively low coke producing operation wherein only a portion of the catalyst circulated in a given reactor system requires regeneration, the different catalyst regeneration operations may be housed in separate or a common regeneration vessel but kept separate from one another.

In a more particular aspect the present invention relates to a multiple zone fluidized catalyst conversion operation such as provided by a plurality of adjacent riser conversion zones maintained at operating conditions to particularly accomplish the restructuring of methanol and derivatives thereof to low and high boiling gasoline boiling range components comprising olefins, aromatics and alkylaromatics. In the combination operation herein identifieid, the reactant or methanol feed is simultaneously processed at both high and low temperature severity operations within the range of 500° to about 1000°F. to particularly accomplish the production of a highly olefinic $C_5/C_6$ aliphatic gasoline blending material as well as the higher boiling alkylaromatics. The catalyst employed is preferably a crystalline zeolite particularly comprising at least a ZSM-5 type of crystalline zeolite dispersed in a suitable matrix material of relatively low cracking activity. For example, in this multiple riser operation, an olefin feed may be reacted with itself at a high or low temperature in one riser and an ether product of methanol conversion may be reacted alone or in combination with methanol in a second riser reactor under conditions particularly promoting the formation of branched olefins and not so many aromatics. The operating embodiments of the present invention contemplate on the other hand, reacting light olefins and light aromatics such as benzene in one conversion zone to form heavier aromatics in a greater volume.

In yet another aspect, the present invention contemplates reprocessing the higher boiling portion of the formed gasoline boiling range material should an undesired amount of durene be found to exist in the product. Thus, it is contemplated reprocessing a durene rich fraction under essentially dealkylating conditions or a mixture comprising benzene, toluene and durene under transalkylation conditions at relatively high temperatures in the range of 700° to about 1100°F. in the presence of a zeolite catalyst in which catalyst a faujasite crystalline zeolite alone or in combination with a ZSM-5 type crystalline zeolite, is the major crystalline zeolite component. In a high temperature transalkylation operation of a mixture of $C_6$ to $C_{10}$ aromatics effected at a reactant residence time within the range of 0.5 to about 10 seconds, a transfer of methyl groups is accomplished particularly reducing the presence of benzene and durene in the product of the operation.

In the combination operation herein discussed, alkylaromatics such as toluene and toluene rich fractions are converted in high selectivity to mixtures rich in xylene and benzene by effecting reaction thereof in a short contact time dilute fluid catalyst phase conversion zone maintained at a relatively high temperature. By alkylaromatic it is intended to include any mononuclear or polynuclear aromatic hydrocarbon that has alkyl substituents in the ring. Typical examples are toluene, trimethylbenzenes and durene all of which are products of the methanol conversion operation herein discussed.

The aromatic disproportionation concept of the present invention provides excellent selectivity to desired liquid product such as benzene and xylenes with relatively small amounts of $C_9+$ methylbenzenes produced, and very small amounts of coke and gas formation. Thus only very small amounts of valuable liquid chemicals are lost to coke and gas. In addition it has been found that greater than equilibrium quantities of paraxylene are formed. The gas phase has been found to be a valuable product since it comprises large amounts of $C_2 - C_4$ olefins plus a preponderance of isobutane. Such a gas is useful as a source of olefins for chemical production or as a feed to an alkylation operation. Another valuable aspect noted is that no expensive hydrogen gas producing operation is needed in the present operation.

The process combination of the present invention allows for continuous throughput at acceptable rates without loss of down stream time for catalyst regeneration. In addition the combination operation operates at a relatively low pressure less than about 100 psig but higher pressure above 100 psig and as high as about 500 psig but not usually above 250 psig may be employed to particularly improve the catalyst regeneration portion of the operation catalyst cascade from one zone to another and reactant material flow. The combination operation permits the highly efficient contact of reactant with catalyst particles and rapid separation of desired product. This problem associated with diffusion, mass transportation and heat transfer are minimized. The combination operation is extremely flexible and particularly suited for varying conversion severity and/or product selectivity since the catalyst and reactant residence time, catalyst/reactant ratio, temperature, catalyst activity and composition can be varied substantially at will within a relatively short time cycle.

DISCUSSION OF SPECIFIC EMBODIMENTS

The following examples illustrate the essence of the processing concepts of the present invention comprising the conversion of methanol and derivatives thereof to desired products.

EXAMPLE 1

Methanol was pumped from a feed buret to the inlet of a feed preheater of a bench scale riser FCC unit. The 500°F. preheated alcohol (methanol) was then admitted to the riser inlet in contact with 1050°F. initially containing 15 wt.% REY crystalline zeolite catalyst (burned white, 67.5 FAI). The riser reactor inlet mix temperature was about 1000°F; ratio of catalyst to methanol was 23.1 (wt/wt); catalyst residence time in the riser was about 4 sec.; riser inlet pressure was 30 psig, and ratio of catalyst residence time to oil residence time was about 1.27. The riser effluent was discharged into a separation zone wherein a vaporous effluent was separated from suspended catalyst (0.137 wt.% carbon). The vaporous products were collected, separated, and analyzed. Data for the operating conditions and overall mass balance are shown in Table 1. Selectivity for the products on an oxygen-compound-free basis is shown in Table 2. The gasoline composition is given in Table 3.

Similar runs but with different operating variables were made at 750°F. (H-591) and 900°F. (H-590) with the REY catalyst initially containing 15 wt.% REY. Also a run at 750°F. with a 2 wt.% REY + 10 wt.% ZSM-5 crystalline zeolite catalyst (H-592) and a run at 800°F. with a 40 wt.% ZSM-5 zeolite catalyst (unsteamed). Data obtained for these runs is also provided in Tables 1, 2 and 3 below.

Table 1

OPERATING CONDITIONS AND YIELD DATA FOR CATALYTIC REACTION OF METHANOL OVER ZEOLITE CATALYST: BENCH RISER UNIT

| Run Number H- | 591 | 590 | 607 | 592 | 614 | Fluidized Dense Bed |
|---|---|---|---|---|---|---|
| Catalyst Description | ←――――15%REY――――→ | | | 2%REY-10% ZSM-5 | 40% ZSM-5 (70:1 SiO$_2$/Al$_2$O$_3$) | 10% ZSM-5 (70:1 SiO$_2$/Al$_2$O$_3$) |
| FAI | | 67.5 | | 48.5 | — | — |
| Operating Conditions | | | | | | |
| Temp. °F., Reactor Inlet | 750 | 900 | 1000 | 750 | 800 | 700°F. |
| Temp. °F., Oil Inlet | 500 | 500 | 500 | 500 | 515 | 60 minute run |
| Temp. °F. Catalyst Inlet | 830 | 1125 | 1050 | 785 | 833 | 0-psig pressure |
| Catalyst/Oil Ratio, wt/wt | 6.6 | 6.9 | 23.1 | 18.8 | 19.6 | 0.52 WHSV(CH$_3$OH) |
| Catalyst Residence Time, sec. | ~2.5 | ~2.1 | ~3.7 | ~4.1 | ~6.4 | .04 moles/N$_2$ per mole CH$_3$OH dilution |
| Oil Linear Velocity (Superficial) ft/sec. | 15.2 | 18.5 | 10.3 | 9.3 | 6 | |
| Moles of Product/Mole (ex-coke) | 1.01 | 1.10 | 1.20 | 1.04 | — | |
| Reactor Inlet Pressure, psig | 30 | 30 | 30 | 30 | 30 | 100cc CH$_3$OH/hr. |
| Reactant Residence Time,sec. | 2.0 | 1.6 | 2.9 | 3.2 | 5 approx. | |
| Carbon on spent catalyst, wt.% | 0.187 | 0.220 | 0.137 | 0.069 | .0784 | |
| Steam Stripping | Yes | Yes | Yes | Yes | No | |
| Dispersion N$_2$(Mole:N$_2$/mole ft) | 0.07 | 0.07 | 0.21 | 0.29 | ~0.2-0.3 | |
| Conversion, CH$_3$OH, wt.% | ~100 | ~100 | ~99 | ~92 | ~97 | ~99 |
| Run Number H- | 591 | 590 | 607 | 592 | 614 | Est. Wt. Bal. Wt.% |
| Est. Wt. Balance, wt.% (No Loss Basis) | | | | | | |
| H$_2$O | 29.83 | 29.30 | 43.30 | 29.62 | 54.2 | 56.62 |
| CH$_3$OH | — | — | .46 | 2.01 | 3.4 | .26 |
| (CH$_3$)$_2$O | 65.56 | 58.25 | 20.83 | 57.40 | 10.3 | .00 |
| H$_2$ | .04 | .49 | .42 | .04 | .05 | .03 |
| C$_1$ | .22 | 2.69 | 3.02 | .24 | .31 | .27 |
| C$_2$= | .23 | .69 | 2.85 | .07 | .95 | 1.10 |
| C$_2$ | .02 | .11 | .28 | .03 | .08 | .09 |
| C$_3$= | .82 | 2.33 | 3.17 | .84 | .93 | 2.51 |
| C$_3$ | .04 | .05 | .79 | .10 | 1.61 | 3.97 |
| C$_4$= | .61 | 1.26 | 4.89 | .69 | 3.15 | 1.63 |
| i-C$_4$ | .31 | .62 | 4.12 | .14 | 5.09 | 6.66 |
| n-C$_4$ | .10 | .20 | .66 | .39 | 1.29 | .95 |
| C$_5$± Gasoline | .51 | 1.28 | 8.32 | 1.10 | 16.69 | 25.59 |
| Cycle Oil | .41 | 1.10 | — | — | 0 | .00 |
| Coke | 1.31 | 1.63 | 3.36 | 1.31 | 1.9 | .32 |
| CO | — | — | 3.56 | — | 0 | .00 |
| Recovery, % | ~70 | ~31 | ~82 | ~84 | 80.5 | 95.89 |

Table 2

| SELECTIVITY BASED ON OXYGEN COMPOUND-FREE BASIS | | | | | | |
|---|---|---|---|---|---|---|
| Selectivity, wt.% | H 591 | H 590 | H 607 | H 592 | H 614 | Fluidized Dense Bed |
| H$_2$ | .87 | 3.9 | 1.32 | .81 | .16 | .07 |
| C$_1$ | 4.77 | 21.6 | 9.48 | 4.85 | .97 | .63 |
| C$_2$= | 4.99 | 5.5 | 8.95 | 1.41 | 2.96 | 2.55 |
| C$_2$ | .43 | 0.9 | .88 | .61 | .25 | .21 |
| C$_3$= | 17.69 | 18.7 | 9.95 | 16.97 | 2.90 | 5.82 |
| C$_3$ | .87 | 0.4 | 2.48 | 2.02 | 5.02 | 9.21 |
| C$_4$= | 13.23 | 10.1 | 15.35 | 13.94 | 9.83 | 3.78 |
| i-C$_4$ | 6.72 | 5.0 | 12.94 | 2.83 | 15.88 | 15.45 |
| n-C$_4$ | 2.17 | 1.6 | 2.07 | 7.88 | 4.02 | 2.20 |

Table 2-continued

SELECTIVITY BASED ON OXYGEN COMPOUND-FREE BASIS

| Selectivity, wt.% | H 591 | H 590 | H 607 | H 592 | H 614 | Fluidized Dense Bed |
|---|---|---|---|---|---|---|
| $C_5+$ gasoline | 11.06 | 10.3 | 26.12 | 22.22 | 52.07 | 59.34 |
| Cycle Oil | 8.89 | 8.8 | — | — | — | 0.00 |
| Coke | 28.31 | 13.0 | 11.18 | 26.46 | 5.93 | .74 |
|  | 100.0 | 99.8 | 100.7 | 100.00 | 99.99 | 100.00 |

Table 3

$C_5+$ Gasoline Composition Data

| Hydrocarbon Class | Wt.-% in $C_5+$ Gasoline | | |
|---|---|---|---|
|  | H-607 Riser | H-614 Riser | Fluidized Dense Bed |
| $C_5-$ olefins | 29.0 | 5.41 | 2.88 |
| iso—Pentane | 41.1 | 24.43 | 13.88 |
| n-Pentane | 4.8 | 3.48 | 1.37 |
| cyclo-Pentane | — | 2.74 | .84 |
| $C_6+$ Paraffins | 15.5 | 20.96 | 17.58 |
| $C_6+$ Olefins | 8.8[a] | 3.03 | 4.06 |
| $C_6+$ Naphthene | — | 5.32 | 6.00 |
| $C_6+$ Aromatics | 0.8 | 34.61 | 53.32 |
|  | 100.0 | 99.98 | 99.93 |
| $C_6+$ Aromatic Aromatic Distribution | Wt.% of Aromatic Fraction | | |
|  | H-607 | H-614 | 173-1-12-46 |
| Benzene | 50 | trace | 0.3 |
| Toluene | 50 | 4.9 | 0.5 |
| $C_9$—Alkyl benzenes | — | 35.0 | 19.6 |
| $C_9$—Alkyl benzenes | — | 36.0 | 40.6 |
| $C_{10}$—Alkyl benzenes | — | 15.1 | 33.6 |
| $C_{11}$—Alkyl benzenes | — | 2.4 | 2.1 |
| Naphthalene | — | 1.0 | 3.3 |
| Other aromatics | — | 5.2 | — |
|  |  | 100.0 | 100.0 |
| (Durene 1,2,4,5-tetramethyl benzene) |  | (4.1) | (16.2) |

[a] Mainly $C_6-$ olefins

EXAMPLE 2

Methanol was pumped (at a rate of 100 cc/hr) from a feed reservoir into a fluidized dense catalyst bed bench scale reactor. The catalyst used was a 10% ZSM-5 (70:1 silica) (alumina ratio, unsteamed) in a silica-clay matrix. The temperature was 700°F; the weight hourly space velocity (W.H.S.V.) was 0.52; the pressure was 0 psig (14.7 psia); and the run duration was about 60 minutes. Nitrogen (at a rate of 0.04 mole/mole of $CH_3OH$) was employed as a diluent. The gaseous and liquid product effluent was separated and analyzed. The catalyst was stripped with $N_2$ after the run. Data for operating conditions and mass balance are given in Table 1. Selectivity on an oxygen-compound-free basis is shown in Table 2, while the gasoline composition is given in Table 3.

EXAMPLE 3

A feedstock consisting of a mixture of durene (20 wt.%) benzene (20 wt.%) and toluene (60 wt.%) was prepared in the laboratory. The mixture showed a specific gravity of 0.8732 at 60°F. The mixture of benzene and toluene (both C.P. Grade) was prepared to simulate a light aromatic gasoline fraction. The durene (98% pure, M.W. 134.22 m.p. 78°–80°C.) represents a troublesome $C_{10}$-alkylbenzene (1,2,4,5-tetramethyl-benzene), which is sometimes formed in significant quantities in the conversion of methanol to gasoline. Durene raises the pour point of the gasoline, will crystallize out at low temperatures and thus act as a sludge, potentially plugging pipes, filters, etc. In the following experiment, the above mixture of durene, benzene and toluene is converted in a bench scale riser FCC to a substantially durene-free, high quality gasoline product with only a trace loss of carbon to gas or coke.

The above described feed mixture was preheated to 423°F. and then admitted to the riser inlet for contact with hot (900°F) 15 wt.% REY crystalline zeolite catalyst (burned-white, 67.5 FAI). The riser reactor inlet mix temperature was about 800°F; ratio of catalyst to change (wt/wt) was 10.12, catalyst residence time was 4.25 seconds, riser inlet pressure was 30 psig, and the ratio of catalyst residence time to reactant mixture residence time (slip) was 1.20. A riser vaporous effluent was obtained separate from the catalyst. The spent catalyst contained 0.07 wt.% carbon. The effluent was separated into gaseous and liquid products, and analyzed. This run is identified as H-662. Data for the operating conditions, mass balance, and gasoline analysis (including the ratios of gasoline alkylaromatics) are shown in Tables 4, 5 and 6, respectively.

EXAMPLE 4

This example is similar to Example 3 except for operating variables including a temperature of 900°F. Data for this example is provided in Tables 4, 5 and 6.

The results obtained are highly significant for the following reasons:

1. In both riser runs, the level of durene in the gasoline product was reduced from a level of about 20 wt.% to levels of about 0.2–0.4 wt.%, a decrease by a factor of 500–100. That is, durene, 1,2,4,5-tetramethyl-benzene in the gasoline product was lowered to insignificant trace levels by the single pass fluid catalyst riser conversion operation at short contact time. The presence of durene at such low levels will cause no problems such as crystallization, precipitation etc., which could lead to plugging, etc.

2. The redistribution of alkyl groups in the reactant mixture was catalytically effected with essentially 98–99 wt.% conservation of carbon as aromatic gasoline, with less than 1 wt.% of total feed going to coke and 0.5 wt.% of the total feed going to gas. That is, in this fuels-oriented transformation, virtually no loss of valuable, high-octane alkyl aromatics to gas or coke was observed.

3. Surprisingly, the separated gas product is a valuable product, since it consisted of only a minor proportion of methane, and large amounts of $C_2$–$C_5$ olefins plus a preponderance of isobutane. The molecular distribution obtained at 800°F. is particularly excellent. Such a product stream is an excellent acid alkylation plant feed, with more than enough isobutane for alkylation stoichiometry.

Table 4

Reaction of Durene with Low Boiling Aromatics Over Zeolite Catalyst

| Reaction Conditions | H-662 | H-663 |
|---|---|---|
| Reactor Inlet Temp., °F. | 800 | 900 |
| Oil Feed Temp., °F. | 423 | 500 |
| Catalyst Inlet Temp., °F. | 900 | 1006 |
| Catalyst/Oil (wt/wt) Ratio | 10.12 | 7.51 |
| Catalyst Residence Time, Sec. | 4.25 | 4.64 |
| Reactor Inlet Pressure, psig. | 30 | 30 |
| Moles of Product/Mole Feed (Ex. Coke) | 0.924 | 0.920 |
| Oil Partial Pressure, Inlet, psia. | 34.9 | 37.8 |
| T mix, °F. | 798 | 870 |
| Carbon, Spent Catalyst, % wt. | 0.07 | 0.118 |
| Slip Ratio | 1.20 | 1.23 |
| Oil Residence Time, sec. | 3.54 | 3.77 |
| Catalyst | | 15% REY[a] |

[a]15 wt.% REY crystalline zeolite, burned white, FAI

Table 5

Analysis of Product Selectivities: Reaction of Durene with Low Boiling Aromatics Over Zeolite Catalysts

| Product Out | Wt.% Products (NLB on feed) | |
|---|---|---|
| | H-662 | H-663 |
| Coke | 0.77 | 0.96 |
| $C_5+$— Gasoline | 98.72 | 98.67 |
| Gas | 0.51 | 0.36 |
| | 100.00 | 99.99 |

| Light Product Breakdown | Wt.% | Wt.% on Gas | | Wt.% on Gas |
|---|---|---|---|---|
| $H_2$ | 0.00 | — | 0.00 | — |
| Methane | 0.01 | 2.0 | 0.03 | 8.1 |
| Ethylene | 0.03 | 5.9 | 0.03 | 8.1 |
| Ethane | 0.00 | — | 0.01 | 2.7 |
| Propylene | 0.04 | 7.8 | 0.02 | 5.4 |
| Propane | 0.10 | 19.6 | 0.07 | 18.9 |
| Butene | 0.10 | 19.6 | 0.06 | 16.2 |
| Isobutane | 0.23 | 45.1 | 0.12 | 32.4 |
| n-butane | 0.00 | — | 0.03 | 8.1 |
| Pentene | 0.05 | 100.0 | 0.02 | 99.9 |
| Isopentane | 0.14 | | 0.08 | |
| n-Pentane | 0.00 | | 0.01 | |
| Recovery, wt.% | 96.02 | | 95.93 | |

Table 6

Gasoline Analyses From Reaction of Durene with Low Boiling Aromatics Over Zeolite Catalyst

| | | Wt.% | |
|---|---|---|---|
| A. TYPE ANALYSIS | Feed | H-662 | H-663 |
| Paraffins | | 0.118 | 0.068 |
| Naphthenes | | 0.003 | 0.003 |
| Aromatics | 100.0 | 99.879 | 99.928 |
| Olefins | | 0.000 | 0.000 |
| | | 100.00 | 99.999 |
| B AROMATIC BREAKDOWN, wt.% of Gasoline | | | |
| Benzene | 20.0 | 16.64 | 16.95 |
| Toluene | 60.0 | 44.80 | 43.93 |
| Ethyl benzene | | .45 | 0.10 |
| para-xylene | | 6.22 | 7.53 |
| meta-xylene | | 12.68 | 12.99 |
| ortho-xylene | | 5.91 | 6.31 |
| Cumene | | .09 | 0.34 |
| 1,3,5-Trimethylbenzene | | 2.86 | 2.61 |
| 1,2,4-Trimethylbenzene | | 7.23 | 6.66 |
| 1,2,3-Trimethylbenzene | | 1.04 | 1.00 |
| Other C-9 alkylbenzenes | | .12 | .11 |
| Durene | 20.0 | .41 | .20 |
| Other Tetramethylbenzenes | | .99 | .68 |
| Other $C_{10}$ Alkylaromatics | | .03 | .01 |
| Other Aromatics | | .30 | .42 |
| | | 100.0 | 99.8 |

Table 6-continued

Comparison of Xylene Isomer Distribution with Equilibrium

| | H-662 | | H-663 | |
|---|---|---|---|---|
| | Observed | Eq.800°F. | Observed | Eq.900°F. |
| p-Xylene | 25.1 | 23.3 | 28.1 | 23.2 |
| m-xylene | 51.1 | 52.2 | 48.4 | 51.7 |
| o-xylene | 23.8 | 24.3 | 23.5 | 25.0 |
| | 100.0 | 99.8 | 100.0 | 99.9 |

EXAMPLE 5

Reaction of Toluene over Zeolite Catalysts

A toluene feedstock (Baker C.P. grade) was pumped to the inlet of a 30 ft. bench scale riser FCC unit. After preheating (to 500°F.) the toluene feed was then admitted to the riser inlet, where hot (991°F.) catalyst (15% REY crystalline zeolite catalyst, burned-white, 67.5 FAI) was admitted and catalytic reaction allowed to occur. Riser reactor inlet and mix temperature were about 900°F., ratio of catalyst to charge (wt/wt) was 8.49, catalyst residence time was 3.85 seconds, riser inlet pressure was 30 psig, and ratio of catalyst residence time to oil residence time (slip) was 1.23. The effluent obtained was then passed through a stripping chamber where a gaseous effluent was separated from the catalyst (0.058 wt.% carbon). The gaseous effluent was cooled and liquid products were collected, separated by fractionation, and analyzed. This run is numbered H-666. Data for the operating conditions, mass balance and liquid product analysis are shown in Tables 7, 8 and 9, respectively.

EXAMPLE 6

Similar to Example 1 except for temperature (1100°F) and other operating variables (Data are also shown in Tables 1, 2 and 3).

EXAMPLE 7

Similar to Example 1, except for catalyst (a 2% REY plus 10% mordenite catalyst was used), temperature (800°F) and other operating variables.

The results obtained are significant since only small amounts of toluene feed were converted to gas (0.3–0.5 wt.%) and coke (0.2–0.7 wt.%). Further, the spent catalysts showed only 0.04–0.08 wt.% carbon, thus minimizing regenerator air and process requirements. Note also the excellent quality of the gas, which consists of only minor proportions of methane, with large amounts of $C_2$–$C_5$ olefins plus a preponderance of isobutane and isopentane. This gas stream would be particularly well suited as a fuels alkylation feed, with more than enough isobutane for alkylation stoichiometry. Most important, substantial quantities of toluene were converted by transalkylation (or disproportionation) to a highly useful mixture of benzene and mixed xylenes. Traces only of ethylbenzene were formed, and a further disproportionation of the formed xylenes to form trimethylbenzenes and high aromatics was very small. Further, greater than equilibrium amounts of para-xylene were formed: (25.4 vs 23.2 wt.% run H-666 and 24.33 vs 22.8 wt.% in run H-674). This favorable xylene isomer ratio permits a more favorable separation in a cryogenic meta-/paraxylene crystallizer-separator.

TABLE 7

REACTION OF TOLUENE OVER ZEOLITE CATALYSTS IN RISER PILOT PLANT FCC

| Run | H-666 | H-674 | H-665 |
|---|---|---|---|
| Reaction Conditions | | | |
| Reactor Inlet Temp., °F. | 900 | 1100 | 800 |
| Oil Feed Temp., °F | 500 | 600 | 500 |
| $T_{mix}$, °F | 871 | 1067 | 807 |
| Riser Inlet Pressure, Psig | 30 | 30 | 30 |
| Catalyst Inlet Temp., °F | 991 | 1218 | 1027 |
| Catalyst/Oil (wt./wt.) Ratio | 8.49 | 8.51 | 3.86 |
| Catalyst Residence Time, sec | 3.85 | 2.78 | 2.71 |
| Oil Residence Time, sec | 3.13 | 2.34 | 2.20 |
| Oil Partial Pressure, Inlet, psia | 37.0 | 37.8 | 38.6 |
| Moles of Product/mole of feed | 0.918 | 0.920 | 0.921 |
| Carbon, Spent catalyst, %-wt. | 0.058 | 0.071 | 0.037 |
| Slip, ratio | 1.23 | 1.19 | 1.23 |
| Catalyst | ←—15% REY[a] in matrix—→ | ←—2% REY[b] + 10% Mordenite—→ | |

[a] Burned white, FAI=67.5
[b] Burned white, FAI=38.6, matrix=silica/clay/ZrO₂; catalyst steamed at 1400°F for 4 hrs.

TABLE 8

ANALYSIS OF PRODUCT SELECTIVITIES AND MASS BALANCE, TOLUENE REACTION OVER ZEOLITE CATALYSTS IN RISER FCC

| Product out | Wt.-% Products (NLB on Feed) | | |
|---|---|---|---|
| | H-666 | H-674 | H-665 |
| Coke | 0.54 | 0.67 | 0.16 |
| C₅+—Liquid | 99.08 | 98.84 | 99.59 |
| Gas | 0.38 | 0.50 | 0.26 |
| | 100.00 | 100.01 | 100.01 |
| Light Product Breakdown | | | |
| H₂ | 0.00 | 0.01 | 0.00 |
| CH₄ | 0.02 | 0.18 | 0.01 |
| Ethylene | 0.04 | 0.10 | 0.01 |
| Ethane | 0.00 | 0.02 | 0.00 |
| Propylene | 0.01 | 0.03 | 0.00 |
| Propane | 0.08 | 0.04 | 0.04 |
| Butene | 0.08 | 0.04 | 0.08 |
| iso-Butane | 0.15 | 0.07 | 0.10 |
| n-Butane | 0.00 | 0.00 | 0.00 |
| Pentene | 0.04 | 0.02 | 0.04 |
| iso-Pentane | 0.07 | 0.05 | 0.11 |
| n-Pentane | 0.02 | 0.01 | 0.02 |
| Recovery, wt.% | 98.27 | 92.93 | 96.28 |
| Conversion of toluene, wt.-% | | | |
| (a) to all other products | 13.11 | 20.79 | 0.96 |
| (b) to other aromatics | 12.19 | 19.62 | 0.54 |

TABLE 9

LIQUID PRODUCT ANALYSIS FROM REACTION OF TOLUENE OVER ZEOLITE CATALYSTS IN RISER FCC

| Type Analysis | Feed | H-666 | H-674 | H-665 |
|---|---|---|---|---|
| Paraffins | | | | 0.016 |
| Olefins | | | | 0.0009 |
| Naphthenes | | | | |
| Aromatics | 100.0 | | | 99.940 |
| Total | 100.0 | | | 99.965 |

| Liquid Product Breakdown, wt.-% | Feed | H-666 | H-674 | H-665 |
|---|---|---|---|---|
| C₅ | | 0.03 | 0.03 | 0.036 |
| Benzene | | 4.83 | 8.57 | 0.1250 |
| Toluene | 100.0[b] | 87.69 | 80.15 | 99.4620 |
| Ethylbenzene | | 0.06 | 0.07 | 0.043 |
| p-xylene | | 1.68 | 2.43 | 0.125 |
| m-xylene | | 3.41 | 5.11 | 0.151 |
| o-xylene | | 1.51 | 2.46 | 0.035 |
| cumene | | 0.00 | | — |
| 1,3,5-trimethylbenzene | | | | — |
| 1,2,4-trimethylbenzene | | 0.79 | 1.19 | — |
| 1,2,3-trimethylbenzene | | | | |
| other C₉-alkylbenzene | | | | — |
| C₁₀-aromatics | | | | — |
| other aromatics | | | | — |
| Total | 100.0 | 100.0 | 100.01 | 99.98 |

Comparison of Xylene Isomer Distribution with Equilibrium[a], wt.-%

| | H-666 | | H-674 | | H-665 | |
|---|---|---|---|---|---|---|
| | Obs. | EQ.900°F | Obs. | EQ.1100 | Obs. | EQ.800°F |
| p-Xylene | 25.4 | 23.2 | 24.33 | 22.8 | 40.3 | 23.4 |
| m-Xylene | 51.7 | 51.8 | 51.09 | 50.5 | 48.5 | 52.3 |
| o-Xylene | 22.9 | 25.0 | 24.57 | 26.7 | 11.2 | 24.3 |
| | 100.0 | 100.0 | 99.99 | 100.0 | 100.0 | 100.0 |

[a] By Interpolation-Extropolation of published data.
[b] Toluene is Bauer, reagant Grade The drawing is a schematic arrangement in elevation of a combination process for converting methanol and products of methanol conversion in a plurality of separate conversion zones to gasoline products and disproportionation products thereof boiling in the gasoline boiling range.

Referring now to the drawing, by way of example, a methanol rich charge material is introduced to the process by conduit 2 and passed to heaters 4 and 5 wherein the methanol is preheated and vaporized. Preheated methanol is then passed by conduit 6 from heater 4 to the bottom inlet of riser 8 wherein it comes in contact with catalyst particles adjusted to a desired temperature and introduced by conduit 10. As mentioned above, the catalyst is preferably a crystalline zeolite containing catalyst which is temperature adjusted to form a mixture or suspension temperature with the preheated methanol of about 400° to 750°F. Thus in this specific example riser reactor 8 is maintained as a relatively low temperature riser reaction zone which is maintained within the temperature range of 500° to about 950°F. The reactant residence time selected to provide the formation of aromatics and particularly C₆ to C₉ aromatics is in contact with catalyst particles in the range of 5 to 15 seconds. The suspension passed through riser 8 is discharged and separated by cyclonic separation means 12 or any other suitable means into a catalyst phase 14 and a vaporous product phase comprising aromatics and lower boiling hydrocarbons. The vaporous product phase is withdrawn by conduit 16. The catalyst phase recovered as a bed of catalyst 14 is stripped in the lower portion of a separator-collector vessel with a suitable stripping gas. The stripped catalyst is withdrawn by conduit 18 and passed to catalyst regeneration as required. In some operations only a portion of this stripped catalyst need be regenerated to maintain a low level of coke on the catalyst. Thus, a portion of the stripped catalyst withdrawn by conduit 18 may be recycled directly to the inlet of riser 8 by conduit means not shown.

Another portion of the methanol feed preheated in furnace 5 is passed by conduit 20 to the bottom inlet of an adjacent riser reactor 22 to which temperature adjusted catalyst is introduced by conduit 24. Riser reactor 22 is maintained under conditions preferably promoting the high temperature conversion of methanol to particularly olefinic products and boiling within the front end boiling range of gasoline boiling material. Thus, the catalyst charged to riser 22 is preferably a high temperature catalyst which when combined with the preheated methanol will form a suspension at a temperature greater than 950°F. and preferably at least about 1000° up to about 1200°F. The suspension formed and passed through riser 22 at the identified high temperature and a short selected residence time usually not above about 5 seconds is thereafter separated by cyclonic means 26 into an olefin rich hydrocarbon phase withdrawn by conduit 28 and a catalyst phase collected as bed 30. The catalyst collected as bed 30 may be stripped before removal as by conduit 32. Since catalyst bed 30 is at a relatively high temperature, it is contemplated cascading a portion of the catalyst withdrawn by conduit 32 to the inlet of riser 8 maintained at a lower operating temperature.

In the combination operation of this invention, a third riser reactor is provided for processing an aromatic rich stream and particularly the higher boiling aromatic materials formed in the process under transalkylation conditions promoting the conversion of benzene, toluene and durene to more desirable aromatic products lower boiling than $C_{10}$ aromatics. Thus the vaporous hydrocarbons in conduits 16 and 28 are combined and passed by conduit 34 to a product fractionator 36. In fractionator 36 a separation is made which permits the recovery of a heavy oil product from the bottom of the fractionator by conduit 38; a heavy aromatic cut comprising $C_{10}$ (durene) withdrawn by conduit 40; a heavy aromatic gasoline fraction comprising $C_8$ to $C_{10}$ aromatics withdrawn by conduit 42 and an overhead fraction lower boiling than $C_8$ aromatics withdrawn by conduit 44. In the arrangement of the drawing, the overhead fraction in conduit 44 is passed to a cooler 46 wherein the temperature of the overhead is reduced to about 100°F. The cooled overhead material is than passed to an overhead accumulator 50 by conduit 48 wherein a rough separation is made into a gaseous phase, a water phase and a hydrocarbon phase. The gaseous phase is withdrawn by conduit 52, passed to compressor 54 wherein the pressure of the gas is raised to about 200 psig. The compressed gaseous phase is then passed by conduit 56 to a light ends separator 58. In light ends separator 58, a fuel gas stream is separated from a gaseous stream comprising $C_2$ to $C_5$ olefins and withdrawn by conduit 60. The $C_2$–$C_5$ olefin stream is withdrawn by conduit 62 and recycled for distribution in either one or both of risers 8 and 22 by conduits 64 and 66 respectively.

The water phase separated in drum 50 is withdrawn by conduit 68, passed to pump 70 and then by conduit 72 to a methanol recovery zone 74. In zone 74 a separation is made between a water phase withdrawn by conduit 76 and a methanol, methyl ether phase withdrawn by conduit 78. The separated methanol and methyl ether phase is recycled for distribution in either one or both of risers 8 and 22 by conduits 80 and 82 respectively.

A hydrocarbon phase is withdrawn from drum 50 by conduit 84 and recycled in part as reflux to the upper portion of the fractionator by conduit 86. The remaining portion of the recovered hydrocarbon phase comprising about a 250°F.-gasoline boiling fraction and comprising a mixture of benzene and toluene is passed by conduit 88 to separation zone 90 wherein a further separation is made to recover water from the hydrocarbon phase. The water separated in zone 90 is withdrawn by conduit 92. The hydrocarbon phase comprising benzene and toluene is withdrawn by conduit 94 and passed all or in part to storage (STG) or to a light ends separation operation not shown. A portion of this withdrawn material may be passed by conduit 96 to the inlet of a third riser reactor 98 discussed more fully below. On the other hand, it is contemplated separating this fraction into a toluene rich fraction in equipment not shown and then passing the toluene rich fraction to riser 88 alone to effect disproportionation thereof in the riser. It is also contemplated providing a fourth riser reactor in the combination operation to accomplish particularly the toluene disproportionation reaction.

The hydrocarbon phase withdrawn from the fractionator by conduit 42 and identified as a gasoline fraction higher boiling than about 250°F. and comprising $C_8$ and higher boiling aromatics but of restricted durene ($C_{10}$) content less than about 1 weight percent is passed to a separation zone 100 wherein a separation is made to recover a water phase withdrawn by conduit 102 from the hydrocarbon phase. The hydrocarbon phase separated from water and comprising desired $C_8$ to $C_{10}$ gasoline boiling material of high octane rating is withdrawn by conduit 104 for passage to storage gasoline blending operations or to further separation facilities not shown. A portion of this hydrocarbon phase in conduit 104 may be passed by conduit 106 to conduit 96 for recycle to the third riser conversion zone.

The $C_{10}+$ hydrocarbon phase separated to concentrate durene therein is withdrawn from fractionator 36 by conduit 40 for passage to separator 108 wherein a further water separation is made to recover water withdrawn by conduit 110 from the $C_{10}+$ hydrocarbon phase. The hydrocarbon phase recovered by conduit 112 is recycled to a third riser conversion zone 98 by conduit 96. The material withdrawn from the bottom of the fractionator by conduit 38 and identified as a heavy oil will contain some catalyst fines therein. It is proposed to pass this material to a catalyst fines recovery zone not shown and return decanted oil recovered therefrom by conduit 114 to the fractionator. A portion of the material in conduit 38 may be passed by conduit 116 to a cooler 118 wherein the temperature of the material is adjusted to about 450°F. before recycle to the fractionator by conduits 120 and 114.

As mentioned hereinbefore, riser reaction zone 98 to which aromatic constituents are passed is essentially an aromatic transalkylation zone in which a benzene-toluene fraction and a durene rich fraction are restructured to provide, for example, toluene and xylene components. On the other hand, riser 48 or another adjacent riser reactor may be employed to accomplish toluene disproportionation as herein defined.

In the combination operation of this invention, a catalyst component similar to or different from that used in risers 8 and 22 is passed to the lower portion of riser 98 by conduit 122. A suspension is formed in the lower portion of the riser with at least the higher boiling aromatic components in the gasoline boiling range with the introduced catalyst under conditions to form a suspension temperature of at least 800°F. and more usually at least 950°F. but not above about 1100°F. A reactant heater, not shown, may be provided in conduit 96 adjacent the riser inlet. The suspension thus formed is caused to pass through the riser at a preferred temperature of about 1000°F. and a hydrocarbon residence time within the range of 1 to 12 seconds. The suspension passed upwardly through riser 98 is separated by cyclonic separating means after discharge from the riser into a hydrocarbon phase withdrawn by conduit 124 communicating with conduit 34 and a catalyst phase collected as catalyst bed 126. The catalyst in bed 126 may be stripped and then withdrawn by conduit 128 for passage to a catalyst regeneration operation not shown.

In the combination operation above described it is contemplated using the same or a different catalyst in each riser reaction zone. On the other hand, it is contemplated using the same catalyst in risers 8 and 22 but a different catalyst in riser 98. Thus risers 8 and 22 may discharge into a common separation vessel separate from that employed for riser 98 or all three risers may be discharged into a common separation vessel. In any of these arrangements it is important to restrict the level of carbonaceous material deposited on the catalyst so that during regeneration thereof, relatively low catalyst regeneration temperatures may be maintained.

In yet another embodiment, it is contemplated maintaining one of the reaction zones as a dense fluid catalyst bed reaction zone. In this arrangement, the formation of alkyl aromatics may be particularly pursued in the dense fluid bed operation in the presence of catalyst separated from the higher temperature riser operations particularly promoting the formation of front end gasoline boiling components. For example, in the arrangement of the drawing, catalyst bed 30 could be employed for the low temperature conversion operation since the high temperature operation is being pursued in the riser 22. Thus the combination operation herein defined contemplates the combination of a multiple riser conversion operation discharging into the same or a different separating-catalyst collecting vessel or a combination operation which uses a fluid bed of catalyst collected in one of the separating vessels to promote the low temperature conversion of methanol to the higher boiling aromatic components of gasoline boiling range material.

In any of the combinations herein identified, it is preferred to employ catalyst regeneration arrangements therewith which are adequate to remove deposited coke from the catalyst and restrict the catalyst regeneration temperature within a relatively low range of about 1000° to 1050°F. It is to be understood also that the temperatures recited for use in riser conversion zones 8, 22 and 98 are those desired for nominal operating pressures within the range of 0 to 30 psig. However, higher pressure may be employed in any one or all of the multiple riser conversion zones and the pressure can be varied over the range of 0 to 300 psig.

Having thus generally described the invention and provided specific examples in support of various operating concepts contemplated thereby, it is to be understood that no undue restrictions are to be imposed by reason thereof except as defined by the following claims.

We claim:

1. In a process for converting methanol by contacting the same over a crystalline zeolite conversion catalyst at elevated temperature, the improvement which comprises passing a methanol-containing charge in contact with said crystalline zeolite conversion catalyst in a conversion zone maintained at a temperature within the range of about 900° to about 1200°F for a reactant to catalyst contact time within the range of 0.5 to 5 seconds to produce an aliphatic product enhancing the front end octane level of gasoline boiling range material, passing another portion of a methanol-containing charge in contact with a crystalline aluminosilicate conversion catalyst in a conversion zone maintained at a temperature within the range of about 500° to about 900°F for a reactant to catalyst contact time within the range of from 10 to 60 seconds so as to provide highly aromatic products boiling in the gasoline boiling range and recovering a product of each of said methanol conversion operations as a combined product of improved octane value over the entire boiling range of gasoline boiling range material.

2. The method of claim 1 wherein unreacted methanol and low boiling olefins are separated from the combined product of the high and low temperature conversion operation and are recycled to one or both of the methanol conversion operations.

3. The method of claim 1 wherein the crystalline zeolite conversion catalyst is selected from the group comprising one or more of faujasite crystalline zeolites, a class of crystalline zeolites represented by ZSM-5 crystalline zeolites mordenite crystalline zeolites.

4. The method of claim 1 wherein the catalyst employed in the higher temperature conversion operation is separated from reaction products and cascaded to the lower temperature conversion operation before effecting regeneration of the cascaded catalyst.

5. The method of claim 1 wherein a different crystalline zeolite conversion catalyst is employed in the higher temperature conversion operation than in the lower temperature conversion operation.

6. The method of claim 1 wherein a faujasite crystalline zeolite is employed as one of the catalyst components and one or both of a crystalline zeolite represented by mordenite and ZSM-5 crystalline zeolite is employed with the faujasite crystalline zeolite.

7. The method of claim 1 wherein the crystalline zeolite is a ZSM-5 crystalline zeolite dispersed in an inorganic oxide matrix.

8. The method of claim 1 wherein the higher temperature conversion operation is effected in a riser conversion zone and the lower temperature methanol conversion operation is effected in a relatively dense fluid catalyst bed conversion zone.

9. The method of claim 1 wherein the catalyst employed in the higher and lower temperature conversion zones is separated from reaction products, a portion of the separated catalyst is passed to catalyst regeneration and the remaining portion thereof is passed to one or both of the conversion zones.

10. The method of claim 1 wherein a separate conversion zone is provided wherein an olefin rich feed is converted to gasoline boiling components in the presence of said crystalline zeolite catalyst at a high or low temperature and an ether product of methanol conversion is converted in a separate conversion zone in the presence of a crystalline zeolite conversion catalyst maintained under conditions particularly promoting the formation of branched olefins.

11. The method of claim 10 wherein light products comprising light aromatics and olefins are separated from the products of the conversion operation and the separated light products are thereafter reacted in a separate conversion zone to form heavier aromatics.

12. The method of claim 1 wherein a $C_6$ to $C_{10}$ aromatic rich product is separated from the products of the methanol conversion operation and the thus separated aromatics are passed in contact with a crystalline zeolite transalkylation catalyst at a temperature within the range of 700° to 1100°F. at a reactant residence time within the range of 0.5 to 10 seconds to effect reactions reducing the concentration of benzene and durene in the product therefrom.

13. The method of claim 11 wherein a toluene rich fraction is separated from the products of the combination operation and thereafter further converted with a crystalline zeolite catalyst to a mixture rich in xylene.

14. The method of claim 12 wherein an isobutane rich product is separated from the products of the combination operation.

15. The method of claim 13 wherein the catalyst employed for toluene disproportionation comprises a rare earth exchanged "Y" faujasite crystalline zeolite in combination with a mordenite crystalline zeolite.

* * * * *

UNITED STATES PATENT OFFICE
CERTIFICATE OF CORRECTION

Patent No. 3,969,426     Dated July 13, 1976

Inventor(s) Hartley Owen et al.     Page 1 of 2

It is certified that error appears in the above-identified patent and that said Letters Patent are hereby corrected as shown below:

Column 7, Table 3    -(a) Mainly $C_6$ - olefins-should be added after "$C_6$+ Aromatics"

Column 8, line 57    - $\angle$ - should be before "0.5 wt.%"

Column 9, Table 4    - "a" 15 wt.% REY crystalline zeolite, burned white, FAI=67.5 - should only be in Column 9 under Table 4, not extending into Column 10

Column 9, Table 5 should appear as shown on the attached sheet.

Signed and Sealed this

Fourteenth Day of December 1976

[SEAL]

*Attest:*

RUTH C. MASON
*Attesting Officer*

C. MARSHALL DANN
*Commissioner of Patents and Trademarks*

Table 5

Analysis of Product Selectivities : Reaction of Durene with Low Boiling Aromatics Over Zeolite Catalysts

| | Wt.% Products (NLB on feed) | | | |
|---|---|---|---|---|
| Product Out | H-662 | | H-663 | |
| Coke | 0.77 | | 0.96 | |
| $C_5^+$- Gasoline | 98.72 | | 98.67 | |
| Gas | 0.51 | | 0.36 | |
| | 100.00 | | 99.99 | |
| Light Product Breakdown | | Wt.% on Gas | | Wt.% on Gas |
| $H_2$ | 0.00 | - | 0.00 | - |
| Methane | 0.01 | 2.0 | 0.03 | 8.1 |
| Ethylene | 0.03 | 5.9 | 0.03 | 8.1 |
| Ethane | 0.00 | - | 0.01 | 2.7 |
| Propylene | 0.04 | 7.8 | 0.02 | 5.4 |
| Propane | 0.10 | 19.6 | 0.07 | 18.9 |
| Butene | 0.10 | 19.6 | 0.06 | 16.2 |
| Isobutane | 0.23 | 45.1 | 0.12 | 32.4 |
| n-butane | 0.00 | - | 0.03 | 8.1 |
| Pentene | 0.05 | 100.0 | 0.02 | 99.9 |
| Isopentane | 0.14 | | 0.08 | |
| n-Pentane | 0.00 | | 0.01 | |
| Recovery, wt.% | 96.02 | | 95.93 | |